United States Patent [19]

Ho

[11] Patent Number: 5,356,292
[45] Date of Patent: Oct. 18, 1994

[54] DENTAL SANDBLASTING CONFINER

[76] Inventor: Phillip P. Ho, 966 Embarcadero del Mar, Goleta, Calif. 93117

[21] Appl. No.: 173,158

[22] Filed: Dec. 23, 1993

[51] Int. Cl.⁵ ............................ A61C 3/02; A61C 1/16
[52] U.S. Cl. ........................................ 433/88; 433/116
[58] Field of Search ................. 433/83, 84, 85, 88, 433/89, 91, 116, 125

[56] References Cited

U.S. PATENT DOCUMENTS

| | | | |
|---|---|---|---|
| 1,682,784 | 9/1928 | Gythfeldt | 433/116 |
| 1,834,726 | 12/1931 | Ozon | 433/116 |
| 3,747,216 | 7/1973 | Bassi et al. | 433/91 X |
| 4,286,950 | 9/1981 | Hawk | 43.3/116 |
| 5,122,153 | 6/1992 | Harrel | 433/91 X |
| 5,197,876 | 3/1993 | Coston | 433/116 |
| 5,199,229 | 4/1993 | Herold et al. | 433/116 X |

FOREIGN PATENT DOCUMENTS 53791  8/1942  Netherlands ............... 433/116

*Primary Examiner*—Gene Mancene
*Assistant Examiner*—Nicholas D. Lucchesi
*Attorney, Agent, or Firm*—Jack C. Munro

[57] ABSTRACT

A dental sandblasting confiner in the form of a flexible walled transparent cup which has an enlarged inlet opening through which is to be conducted the dispensing nozzle and tip of the sandblasting tool. Included within the cup and opposite the inlet opening is an access opening which is to surround a portion of the tooth that is to be repaired. Also included within the cup is an outlet opening with dispensed sand from the sandblasting tool to be discharged through the outlet opening.

6 Claims, 1 Drawing Sheet

DENTAL SANDBLASTING CONFINER

BACKGROUND OF THE INVENTION

1) Field of the Invention

The field of this invention relates to dental tools and more particularly to a cup for confining and discharging dispensed sand from a sandblasting tool used to perform a drilling operation on a tooth.

2) Description of the Prior Art

Sandblasting has long been known to be an effective technique performing work against an object. Sandblasting has long been used in the construction field on cement block and stucco to remove graffiti and other stains. The same technique in recent years has been applied to a dental tool with the dental tool having a very small outlet opening which discharges a thin stream of fine sand at a high velocity. When this stream of fine sand is directed to a particular section of a tooth, such as a cavity, the abrasive nature of the sand will in essence drill away at the tooth and roughen the tooth surface. This type of sandblasting technique is especially advantageous in porcelain and composite repair as well as increasing the bond of dental composites to metal. This sandblasting technique is currently in use as a drill.

One disadvantage with sandblasting the tooth within the mouth of a human is that the dispensed sand is merely discharged within the entire mouth of the human. It is difficult to remove all of this sand even by multiple rinsings of the mouth of the human after the sandblasting procedure has ended. It would be preferable to remove the sand after it has been dispensed without it being freely thrown into all areas of the mouth of the human.

SUMMARY OF THE INVENTION

The structure of the present invention is directed to a sandblasting confiner in the form of a transparent, flexible walled cup. This cup has an enlarged inlet opening located at one end with a much smaller access opening located within the body of the cup directly opposite the inlet opening. The cup has a longitudinal center axis which connects both the center point of the inlet opening and the center point of the access opening. In between the access opening and the inlet opening is located an outlet opening. A tubular sleeve is attached to the cup about this outlet opening. This tubular sleeve is slanted relative to the cup so as to be located at an obtuse angle relative to the access opening and at an acute angle relative to the inlet opening. The flexibility of the cup is so as to somewhat tightly conform the forward end of the sandblasting tool from which extends the sandblasting dispensing nozzle which ends in a tip.

The primary objective of the present invention is to construct a dental tool in the form of a sandblasting confiner so as to confine dispensed sand during a dental sandblasting technique and discharge such exteriorly of the mouth of the human, not permitting the sand to contaminate areas of the human mouth.

Another objective of the present invention is to construct a dental tool which can be manufactured inexpensively and therefore sold to the dental profession at a reasonable cost.

DESCRIPTION OF THE SHOWN EMBODIMENT

Figure 1:
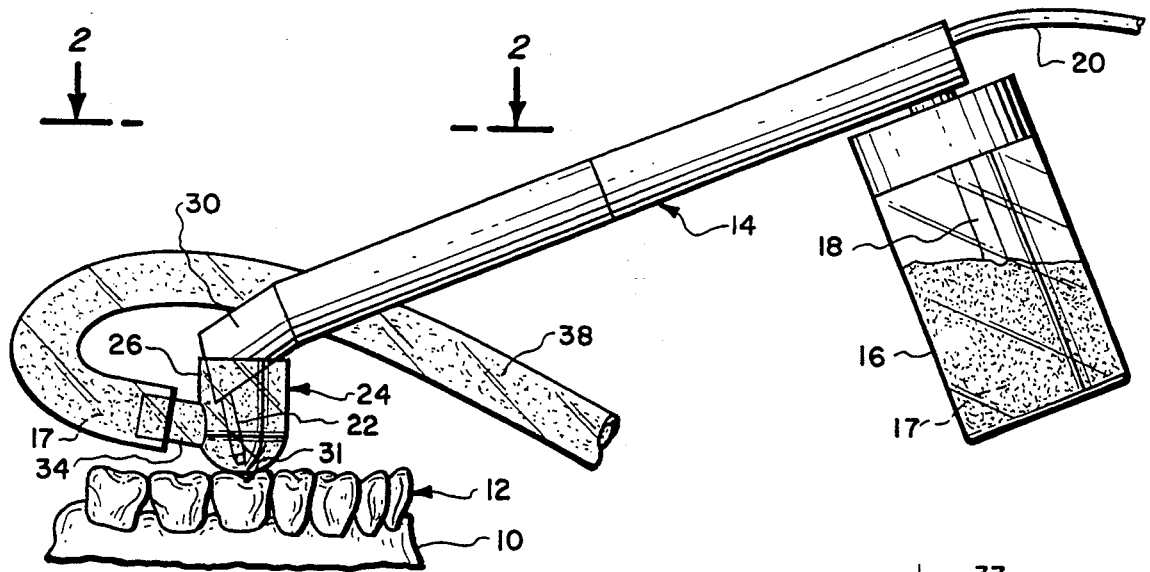
FIG. 1 is a side elevational view of a typical sandblasting tool showing the tool to be mounted in conjunction with the sandblasting confiner of the present invention.
Figures 2, 4:
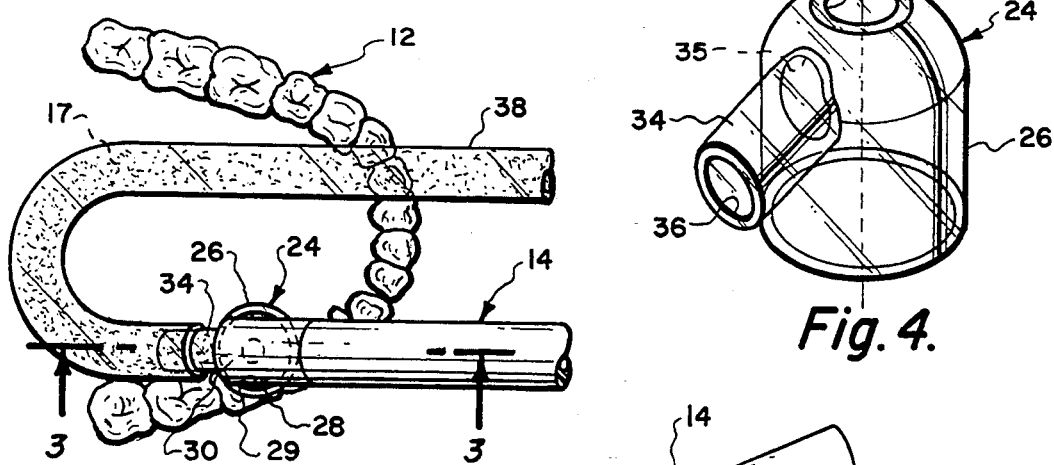
FIG. 2 is a top plan view taken along line 2—2 of FIG. 1.
FIG. 4 is a bottom side, isometric view of the sandblasting confiner of the present invention.

Referring particularly to the drawing, there is shown gum 10 of a human mouth upon which are mounted a plurality of teeth 12. Within one of the teeth 12 is located a cavity 31. A sandblasting tool 14, which is deemed to be conventional, has a reservoir 16 within which is located a quantity of fine sand 17. Extending within the container 16 is a tube 18 with air pressure being supplied to the tool 14 through tube 20 and into container 16. The sandblasting tool 14 terminates at a forward end 30 from which extends in a transverse direction a dispensing nozzle 22. The nozzle 22 is substantially smaller in the transverse cross-sectional area than the forward end 30 as is clearly shown in FIGS. 1 and 3 of the drawing. Upon activation of the tool 14, the sand 17 is to be removed from the container 16 through the tube 18 and then be dispensed in a fine stream under significant amount of pressure through nozzle 22 and exteriorly of the tip 25 of the nozzle.

The sandblasting confiner 24 of the present invention is in the form of a cup 26. In cup 26 is internal chamber 28. Access into the internal chamber 28 is provided through an inlet opening 29 with the forward end 30 connecting with the inlet opening 29. The cup 26 is constructed of plastic and is capable of deflecting so as to conform to the noncircular configuration of the forward end 30. This conforming is in a reasonably snug manner substantially closing off the internal chamber 28. This flexibility of the cup 26 is depicted between the solid line position and the dotted line position shown in FIG. 5.

Cup 26 has a longitudinal center axis 33. This longitudinal center axis 33 passes through the center point of the inlet opening 29 and also through the center point of an access opening 32. Basically, the plane of the access opening 32 is parallel to the plane of the inlet opening 29. The access opening 32 is of substantially smaller diameter than the inlet opening 29. The reason for this is that generally only a quite small area will be operated on on a tooth 12 so there is no need to have an enlarged access opening 32. The access opening 32 is to be located in a surrounding manner around the cavity 31 as is clearly shown in FIG. 3 of the drawings. The cup 26 and the access opening 32 are merely placed as best as possible in a confining manner about the cavity 31 and held in that manner by the dentist or dental technician.

Figures 3, 5:
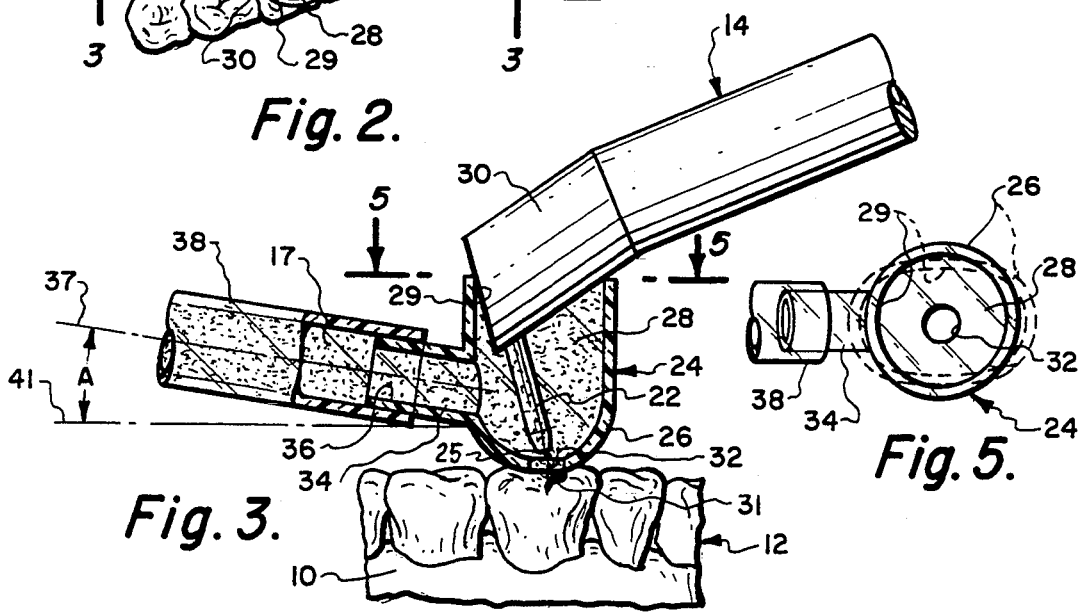
FIG. 3 is a cross-sectional view taken along line 3—3 of FIG. 2 depicting usage of the sandblasting tool in conjunction with the sandblasting confiner of the present invention.
FIG. 5 is a top view of the sandblasting confiner of the present invention taken along line 5—5 of FIG. 3 showing clearly the flexibility permitted in the wall of the sandblasting confiner in the area of the inlet opening.

Connecting with the cup 36 is an outlet opening 35. Surrounding the outlet opening 35 and integrally connected with the cup 26 is a sleeve 34. The sleeve 34 has a longitudinal through hole 36. A discharge tube or hose 38 is to snugly connect with the sleeve 34 as is shown in FIG. 3 of the drawing.

It is to be noticed that the longitudinal center axis 37 of the sleeve 34 is located at an angle A relative to horizontal line 41 which would be located perpendicular to the longitudinal center axis 33. Preferably the angle A should be between ten and fifteen degrees. The purpose of this is so that the sleeve 34 and the discharge hose 38 points upwardly away from the teeth 12 so as to not interfere with the teeth 12. Also this canting of the sleeve 34 will permit the cup 26 to be moved to various angles with the sleeve 34 and the hose 38 not interfering with this locating of the access opening 32 in a particular unusual position.

With the hose 38 connecting with the sleeve 12, the access opening 32 is to be located in a surrounding manner about a cavity 31. Dentists will then take the tool 14 and locate the tip of the nozzle 22 directly adjacent cavity 31 and the access opening 32. This locating is observable by the dentist since the cup 36 is transparent. At the same time the inlet opening 29 will conform in a reasonably snug manner with the forward end 30 of the sandblasting tool 14. The sandblasting tool 14 is then activated with the sand 17 being dispensed and confined within the internal chamber 28. The hose 38 is to be connected to a vacuum so that suction is to be applied through the hose 38 within the internal chamber 28 removing the sand 17 therefrom, pulling such through the outlet opening 35, through hole 36 and through the hose 38 to a discharge location (not shown).

What is claimed is:

1. In combination with a dental sandblasting tool comprising a housing terminating in a forward end, a nozzle extending outward from said forward end, said nozzle having a free outer end defined as a tip, said nozzle being substantially smaller in cross-sectional area than said forward end, sand to be discharged from said tip of said nozzle, a sandblasting confiner to be used with said sandblasting tool as it is operated, said sandblasting confiner comprising:

a flexible walled cup having an internal chamber, said cup having an inlet opening and an outlet opening, said forward end of said sandblasting tool adapted to connect with said inlet opening causing said cup to slightly deform and form a reasonably snug fit when engaged and pressed by said forward end, said cup having an access opening spaced from both said inlet opening and said outlet opening, said tip of said nozzle adapted to be located directly adjacent said access opening when said nozzle with a portion of a tooth is inserted in said cup to be repaired being surrounded by said access opening, said nozzle adapted to be slightly movable relative to the tooth when said nozzles is within said internal chamber while said cup maintains said snug fit with said forward end, whereby as sand is discharged from said tip against the portion of the tooth the sand is confined within said internal chamber and then removed therefrom through said outlet opening.

2. The combination as defined in claim 1 wherein: said cup is transparent.

3. The combination as defined in claim 1 wherein: said outlet opening is of a smaller size than said inlet opening.

4. The combination as defined in claim 1 further comprising:

a sleeve connected to said cup at said outlet opening, wherein a discharge hose is connected to said sleeve through which sand is to be discharged.

5. The combination as defined in claim 4 wherein: said cup is transparent.

6. The combination as defined in claim 5 wherein: said outlet opening is of a smaller size than said inlet opening.

* * * * *